US009567502B2

(12) United States Patent
Bressler et al.

(10) Patent No.: US 9,567,502 B2
(45) Date of Patent: Feb. 14, 2017

(54) POLYMERS AND PLASTICS DERIVED FROM ANIMAL PROTEINS

(71) Applicants: David Curtis Bressler, Edmonton (CA); Phillip Choi, Edmonton (CA)

(72) Inventors: David Curtis Bressler, Edmonton (CA); Phillip Choi, Edmonton (CA)

(73) Assignee: THE GOVERNORS OF THE UNIVERSITY OF ALBERTA, Edmonton (CA)

( * ) Notice: Subject to any disclaimer, the term of this patent is extended or adjusted under 35 U.S.C. 154(b) by 0 days.

(21) Appl. No.: 14/805,985

(22) Filed: Jul. 22, 2015

(65) Prior Publication Data

US 2016/0160048 A1    Jun. 9, 2016

Related U.S. Application Data

(63) Continuation-in-part of application No. 14/117,193, filed as application No. PCT/CA2012/000458 on May 14, 2012, now Pat. No. 9,120,845.

(60) Provisional application No. 61/485,748, filed on May 13, 2011.

(51) Int. Cl.
| | | |
|---|---|---|
| *C09J 189/04* | (2006.01) | |
| *C07K 1/12* | (2006.01) | |
| *C08L 89/00* | (2006.01) | |
| *C08H 1/00* | (2006.01) | |
| *C09J 189/00* | (2006.01) | |
| *C09J 189/06* | (2006.01) | |
| *C08L 89/04* | (2006.01) | |
| *C08L 89/06* | (2006.01) | |
| *C09D 163/00* | (2006.01) | |

(52) U.S. Cl.
CPC ............... *C09J 189/04* (2013.01); *C07K 1/12* (2013.01); *C08H 1/00* (2013.01); *C08L 89/00* (2013.01); *C08L 89/04* (2013.01); *C08L 89/06* (2013.01); *C09D 163/00* (2013.01); *C09J 189/00* (2013.01); *C09J 189/06* (2013.01)

(58) Field of Classification Search
CPC ............ C07K 1/12; C08L 63/00; C08L 89/00; C08L 89/04; C08G 12/46; C08J 3/24; C08J 2389/00; C09J 189/00; C09J 189/04; C08H 1/00
See application file for complete search history.

(56) References Cited

U.S. PATENT DOCUMENTS

| | | | | |
|---|---|---|---|---|
| 4,649,064 A | * | 3/1987 | Jones | .................. B41M 5/5236 346/96 |
| 4,861,698 A | * | 8/1989 | Hiruma | .................. B41N 1/003 101/457 |
| 7,183,453 B2 | | 2/2007 | Wilson | |
| 7,829,755 B2 | | 11/2010 | Wilson | |
| 7,910,788 B2 | | 3/2011 | Wilson | |
| 8,361,501 B2 | * | 1/2013 | DiTizio | ................ A61K 9/7007 424/484 |

OTHER PUBLICATIONS

Apostolov, A., et al.; Journal of Applied Polymer Science, 2000, p. 2041-2048.*
Lai, J.Y.; Journal of Materials Science: Materials in Medicine, 2010, p. 1899-1911.*
Martucci, J.F., et al.; Materials Science and Engineering, 2006, p. 681-686.*
Sigma Aldrich, Gelatin Product Data Sheet, p. 1-3, Accessed Mar. 3, 2016.*
ASTM D2339-98 (Reaproved 2011), Standard Test Method for Strength Properties of Adhesives in Two-Ply Wood Construstion in Shear by Tension Loading ASTM, West Conshohocken.
CFIA. 2009 Bovine Spongiform Encephalopathy, Manual of Procedures, Chapter 5.4.1.
Park S.K., Bae D.H., Hettiarachchy N.S.; Protein Concentrate and Adhesives from Meat and Bone Meal; JAOCS 77 (11), 1223-1227; 2000.

* cited by examiner

*Primary Examiner* — Robert Jones, Jr.
(74) *Attorney, Agent, or Firm* — Bennett Jones LLP

(57) ABSTRACT

The invention is directed to a method for preparing a polymer derived from an animal protein, such as in a feedstock derived from animal by-products. The method involves hydrolyzing proteins present in a feedstock to obtain hydrolyzed proteins, wherein hydrolysis is conducted under conditions sufficient to digest the proteins and destroy pathogens; extracting a protein fraction from the hydrolyzed proteins; and treating the protein fraction with a crosslinking reagent to form the polymer. The crosslinking reagents may include epoxies. The polymer may be further processed to form a thermoset plastic. The polymer may be used as an adhesive, or in the preparation of a natural fiber composite material.

7 Claims, 14 Drawing Sheets

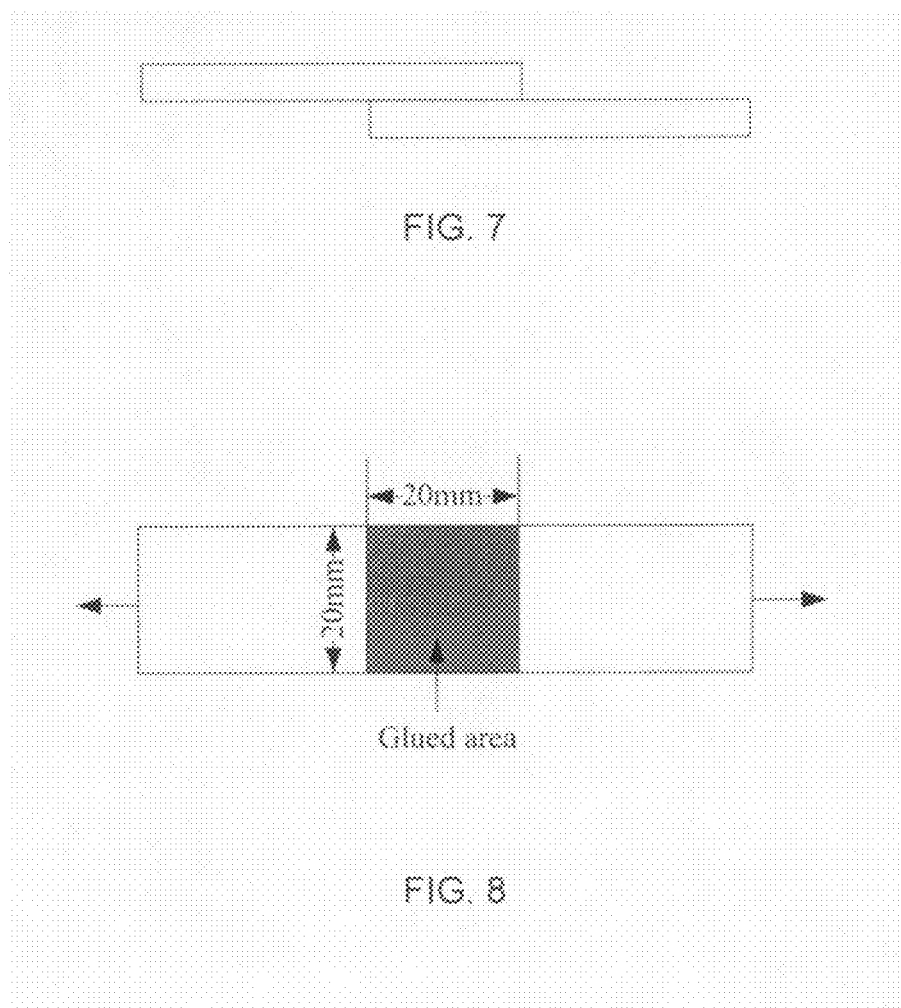

POLYMERS AND PLASTICS DERIVED FROM ANIMAL PROTEINS

CROSS REFERENCE TO RELATED APPLICATIONS

This application is a continuation-in-part of U.S. patent application Ser. No. 14/117,193 which is a national phase application of PCT/CA2012/000458 filed on May 14, 2012, which claimed priority to U.S. Provisional Patent Application 61/485,748 filed on May 13, 2011, the entire contents of each which is incorporated herein by reference.

FIELD OF THE INVENTION

The invention relates to polymers and plastics derived from animal proteins.

BACKGROUND OF THE INVENTION

Transmissible spongiform encephalopathies (TSEs) are progressive, fatal diseases affecting the nervous system, causing spongy degeneration in the brain and spinal cord. TSEs include bovine spongiform encephalopathy (BSE or mad cow disease) in cattle, scrapie in sheep, chronic wasting disease in deer and elk, and variant Creutzfeldt-Jakob disease (vCJD) in humans. Although the exact cause of TSEs is unknown, the infectious agent is suspected to be a prion, a misfolded protein which has the ability to self-replicate and accumulate in neural tissue, eventually causing tissue damage and cell death. There is no treatment or vaccine currently available for the disease. Prions are notoriously resistant to routine methods of decontamination.

BSE was first diagnosed in 1986 in the United Kingdom where the majority of the world's cases have occurred. The first North American cases were discovered in 2003. Consumption by cattle of BSE-contaminated ruminant proteins in animal feed has been cited as the most likely means of transmission. Such outbreaks have had major implications for the North American beef industries since foreign markets have closed their borders to beef and cattle exports. Surveillance programs to monitor and assess BSE in cattle herds have been implemented to provide early detection and contain any possible spread in order to keep BSE out of the food supplies of both animals and humans. In humans, vCJD is thought to be linked to the consumption of meat products derived from BSE-infected cattle.

Prior to the emergence of BSE, the primary use for animal protein by-products was as feed ingredients for cattle, poultry, pets and aquaculture in the form of meat and bone meal, meat meal and blood meal. Subsequently, specific cattle tissues, known as specified risk materials (SRM), have been banned from use in animal feed, pet food and fertilizers, and have been accumulating into landfills at a rate of about 5000 tons per week.

Rendering is a process whereby waste is "cooked" into ingredients for a wide range of industrial and consumer goods. Regulatory actions to strengthen safeguards against BSE portend significant changes in renderer's business practices, and the value of their products. If inedible animal byproducts have fewer market outlets, the overall economic value of the animal to the producer can decline, and questions arise about how to safely dispose of the SRM. The necessary restructuring of the rendering processing lines to handle SRM and non-SRM in separate lines and costs associated with SRM storing, transporting, and disposal fees have adversely affected profitability to operators and negatively impacted the beef industry.

Therefore, there is a need in the art for methods of safely handling SRMs and converting animal byproducts into useful products.

SUMMARY OF THE INVENTION

The present invention relates to polymers and plastics derived from animal proteins, and, in particular, animal proteins derived from byproducts.

In one aspect, the invention comprises a method for preparing a polymer derived from a feedstock comprising animal proteins, comprising the steps of:
 a) hydrolyzing the proteins to produce a hydrolyzed protein mixture; and
 b) treating the hydrolyzed protein mixture with a cross-linking reagent to obtain the polymer.

In one embodiment, the method further comprises the step of treating the hydrolyzed protein mixture to extract a protein fraction.

In one embodiment, the animal proteins comprise a fresh meat carcass, a biological tissue, blood meal, meat, bone meal, or a specified risk material, or combinations thereof. In one embodiment, the animal protein comprises a specified risk material, which may comprise tissues such as brain, skull, eyes, trigeminal ganglia, spinal cord, vertebral column, dorsal root ganglia, tonsils, the distal ileum of the small intestine, or combinations thereof. In one embodiment, the animal proteins may be at risk of contamination of a pathogen which may comprise a bacteria, virus, fungi, parasite, or prion.

In one embodiment, the hydrolysis step comprises thermal hydrolysis. For example, the animal proteins may be subjected to temperatures of at least about 180° C. and at a pressure of about 1,200 kPa.

In one embodiment, the hydrolysis step comprises alkaline hydrolysis where the proteins are hydrolyzed in the presence of a base. In one embodiment, the base comprises an aqueous solution of an alkali metal hydroxide or an alkaline earth metal hydroxide. In one embodiment, alkaline hydrolysis may take place under elevated temperature and pressure. For example, the alkaline hydrolysis may be conducted at a temperature of about 150° C. and at a pressure of about 400 kPa. In one embodiment, a substantial portion of the hydrolyzed proteins produced by alkaline hydrolysis has a molecular weight of less than 35 kDa.

In one embodiment, the crosslinking reagent comprises glutaraldehyde, glyoxal, resorcinol, benzaldehyde, 1-ethyl-3-(3-dimethylaminopropyl)carbodiimide, N-hydroxysuccinimide, N,N-dicyclohexylcarbodiimide, or an epoxy. In one embodiment, the crosslinking reagent is an epoxy such as a diglycidyl ether of bisphenol A, aliphatic polyglycol epoxy, or resorcinol diglycidyl ether.

In one embodiment, the method further comprises the step of blending the polymer with a natural or synthetic rubber.

In another aspect, the invention comprises a polymer comprising hydrolyzed specified risk material (SRM) proteins cross-linked by a cross-linking agent.

In one embodiment, the cross-linking agent comprises glutaraldehyde, glyoxal, resorcinol, benzaldehyde, 1-ethyl-3-(3-dimethylaminopropyl)carbodiimide, N-hydroxysuccinimide, N,N-dicyclohexylcarbodiimide, or an epoxy.

In one embodiment, the hydrolyzed SRM proteins have an average molecular weight of less than about 100 kDa.

In one embodiment, the hydrolyzed SRM proteins have an average molecular weight of less than about 70 kDa.

In one embodiment, the hydrolyzed SRM proteins have an average molecular weight of less than about 35 kDa.

In one embodiment, the polymer is blended with a natural or synthetic rubber.

In another aspect, the invention comprises a thermoset plastic comprising a polymer comprising cross-linked hydrolyzed SRM proteins.

Additional aspects and advantages of the present invention will be apparent in view of the description, which follows. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will now be described by way of an exemplary embodiment with reference to the accompanying simplified, diagrammatic, not-to-scale drawings:

FIG. 7 is a side view of a specimen for testing the adhesive bond strength of a proteinacious adhesive formulation of the present invention.

FIG. 8 is a top view of a specimen for testing the adhesive bond strength of a proteinacious adhesive formulation of the present invention.

DETAILED DESCRIPTION OF PREFERRED EMBODIMENTS

The present invention relates to polymers and plastics, and methods for preparing same from animal proteins.

When describing the present invention, all terms not defined herein have their common art-recognized meanings. To the extent that the following description is of a specific embodiment or a particular use of the invention, it is intended to be illustrative only, and not limiting of the claimed invention. The following description is intended to cover all alternatives, modifications and equivalents that are included in the spirit and scope of the invention, as defined in the appended claims.

Figure 1:
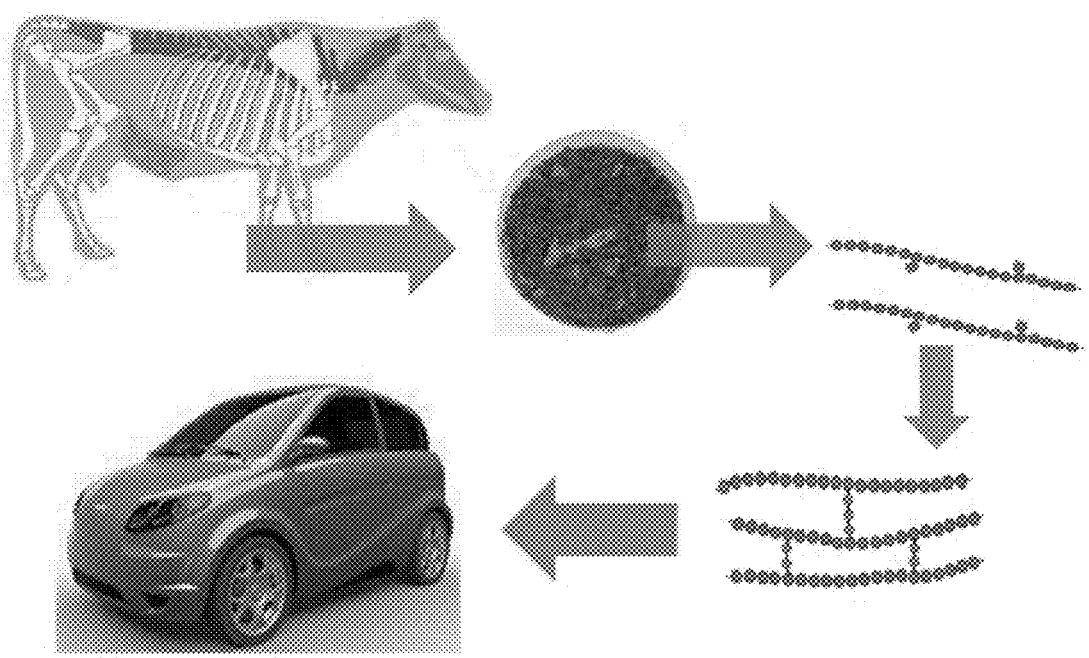
FIG. 1 is a schematic diagram showing one embodiment of the method of the present invention.

As shown generally in FIG. 1, one embodiment of the method utilizes an agricultural byproduct stream as a source of animal proteins, which are modified to form crosslinked polymers having desirable physical and chemical properties. In one embodiment, the crosslinked polymers are further processed to form thermoset bioplastics. Conventionally, a thermosetting polymer is a prepolymer in a soft solid or viscous state that changes irreversibly into an infusible, insoluble polymer network by curing. Curing can be induced by the action of heat or suitable radiation, or both. A cured thermosetting polymer is called a thermoset.

In one embodiment, the invention comprises a method for preparing a polymer derived from a feedstock comprising animal proteins, comprising the steps of:

a) hydrolyzing the proteins to produce a hydrolyzed protein mixture;

b) treating the hydrolyzed protein mixture with a crosslinking reagent to obtain the polymer.

In one embodiment, the invention further comprises the step of treating the hydrolyzed protein mixture to extract a protein fraction, and treating the protein fraction with the crosslinking reagent.

Figure 2:
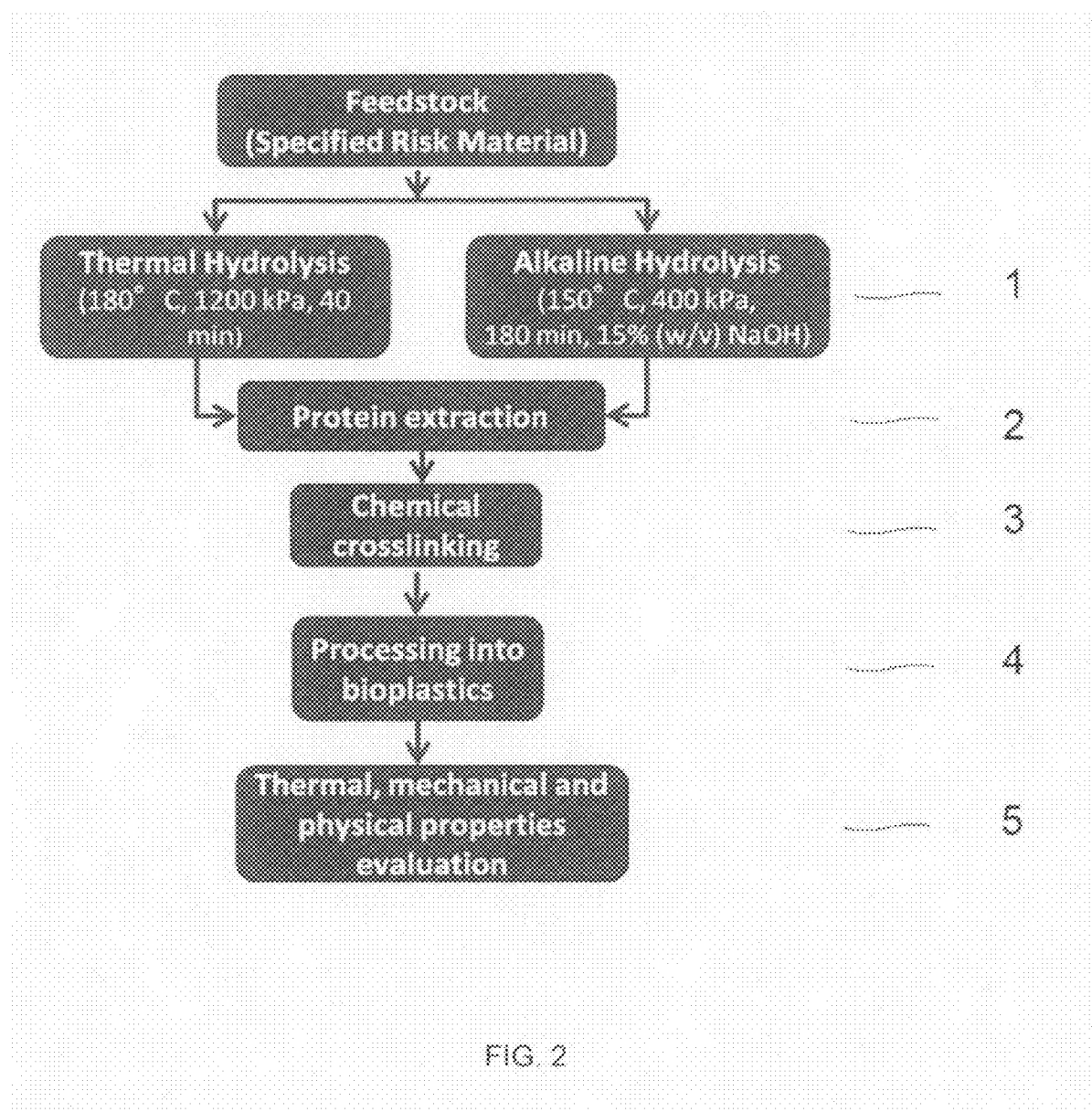
FIG. 2 is a schematic diagram showing one embodiment of the method of the present invention.

As shown in FIG. 2, the polymers are produced from animal proteins using the methods described herein. The method generally involves at least the following sequential steps: (1) hydrolyzing the proteins in a feedstock to yield hydrolyzed proteins using a process such as either thermal hydrolysis or alkaline hydrolysis; (2) extracting a protein fraction from the hydrolyzed proteins, and (3) treating the protein fraction with a crosslinking reagent to obtain crosslinked thermosetting polymers having physical and chemical characteristics comparable to those of products from non-renewable feedstock. The crosslinked polymers may be further processed to obtain thermoset plastics (4). The thermal, mechanical and physical properties of the resultant plastics may be evaluated to assess their suitability for particular applications (5).

The detailed steps of the process are as follows. A feedstock containing animal proteins is used as the starting material. As used herein, the term "feedstock" means an animal product which comprises proteins. Feedstock may include fresh meat carcasses or other animal tissues, such as blood meal (i.e., the dried blood left over after carcasses are processed at a rendering plant), meat, bone meal, and specified risk material. The feedstock may be contaminated with, or at risk of contamination with infectious agents which may include, but not limited to, bacteria, viruses, fungi, parasites, and prions. As used herein, the term "prion" means a proteinaceous-infectious agent which causes transmissible spongiform encephalopathies in humans and animals.

As used herein, the term "specified risk material" means tissues removed from animals slaughtered for human consumption and within which infectious agent may be present. Specified risk material includes, but is not limited to, the brain, skull, eyes, trigeminal ganglia, spinal cord, vertebral column, dorsal root ganglia, tonsils, the distal ileum of the small intestine, and combinations thereof.

The feedstock is preferably a waste material which is typically disposed of or used in a rendering plant. In one embodiment, the feedstock may be processed to reduce particle size if necessary, such as by hammermilling, chopping, grinding or blending. A reduced particle size may facilitate the hydrolysis step which follows.

The first step of the process involves hydrolyzing the proteins in the feedstock to obtain hydrolyzed proteins. As used herein, the term "hydrolyze" refers to the cleavage of amide bonds in a polypeptide to produce carboxylic acid groups and amino groups. Hydrolysis of the proteins generally results in the production of proteins and peptides with varying molecular weight, as well as free amino acids. As used herein, the term "hydrolyzed protein" is the mixture of proteins, peptides, and/or free amino acids produced by the hydrolysis of the proteins present in the feedstock. In one embodiment, hydrolysis comprises thermal hydrolysis or alkaline hydrolysis, or a combined alkaline thermal hydrolysis. Either hydrolytic method is used to safely convert specified risk material into a safe feedstock, with any infectious agents being inactivated or destroyed.

In one embodiment, thermal hydrolysis is conducted at a temperature of at least about 180° C., and at a pressure of about 1,200 kPa. In one embodiment, duration of thermal hydrolysis is at least about forty minutes. Thermal hydrolysis may be conducted in a suitable thermal hydrolysis reactor which uses high pressure and saturated steam to denature organic material and destroy pathogens. Suitable reactors and their operation are well known in the art and need not be further described herein (see for example, vessels manufactured by Haarslev Inc., Kansas City, Mo., USA; or Dupps Company, Germantown, Ohio, USA).

In one embodiment, hydrolysis of the proteins is conducted in the presence of a base. In one embodiment, the base comprises an aqueous solution of an alkali metal hydroxide or an alkaline earth metal hydroxide. In one embodiment, the base comprises an aqueous solution of sodium hydroxide (NaOH) or potassium hydroxide (KOH). In one embodiment, the solution is calculated on a mass per mass basis equal or greater than about 9% of the feedstock. In one embodiment, the solution comprises about 15% sodium hydroxide (w/v) in water or about 19% potassium hydroxide (w/v) in water. In one embodiment, alkaline hydrolysis is conducted at a temperature of at least about 150° C., and at a pressure of at least about 400 kPa. In one embodiment, duration of alkaline hydrolysis is at least about 180 minutes per cycle.

Alkaline hydrolysis may be conducted in any enclosed pressure vessel as are known in the art. The vessel allows the immersion of the feedstock in the alkali which is then heated. The feedstock remains within the alkali until sufficiently digested to inactivate or destroy any pathogens which might be present, thereby forming a solution void of such agents. Suitable vessels are described, for example, in U.S. Pat. Nos. 7,910,788; 7,829,755; and 7,183,453; or may include, but are not limited to, the $WR^2$ alkaline hydrolysis Tissue Digestors™ manufactured by BioSAFE Engineering (Brownsburg, Ind., USA).

Without being bound to any theory, the alkali-catalyzed breaking of the peptide bonds and the addition of water at the break occurs under the above conditions, promoting rapid dissolution and hydrolysis of the proteins into small peptides and amino acids in the form of their sodium or potassium salts.

The conditions and type of hydrolysis may be chosen by one skilled in the art to produce a hydrolyzed protein having a desired degree of hydrolysis. In one embodiment, the hydrolyzed protein will have an average molecular weight of less than about 100 kDA, or 80 kDA, or 70 kDA, and preferably greater than about 1 kDA, 5 kDA, or 10 kDA. Obviously, more severe hydrolysis will produce relatively smaller peptides and more individual amino acids. Less severe hydrolysis will produce relatively larger peptides. Substantially all proteins subjected to alkaline hydrolysis with elevated heat and pressure are severely hydrolyzed to an average molecular weight less than about 40 kDa. Proteins subjected to thermal hydrolysis have a comparatively bigger and wider range of molecular weight with the average being below 70 kDa. The molecular sizes of both the thermal and alkaline hydrolyzed proteins were significantly reduced as the concentration of water and alkaline solution per weight of the feedstock increases, respectively during hydrolysis.

After hydrolysis, a protein fraction is extracted or separated from the hydrolyzed proteins using a combination of salts to promote the precipitation of ash or other impurities which may be detrimental to crosslinking, and selectively retain the protein fraction in aqueous solution. In one embodiment, the salt solution comprises 4% (w/v) NaCl and 0.05% (w/v) $MgCl_2$ (w/v) in a phosphate buffer, comprising 0.067 M $KH_2PO_4$ and 0.067 M $Na_2HPO_4$, according to the method optimized by Park et al (2000) for meat and bone meal. The aqueous protein fraction comprises major active functional groups such as, for example, primary amine (—$NH_2$), carboxyls (—COOH), sulfhydryls (—SH), hydroxyl (—OH), and carbonyls (—CHO). The major active functional groups are positioned on the side chains of amino acids or at the amino or carboxy end of each amino acid chain. In one embodiment, the invention comprises the protein fraction obtained by the method described herein.

The protein fraction is then treated with a crosslinking reagent which reacts with the active functional groups to form crosslinked polymers. Suitable crosslinking reagents include, but are not limited to, glutaraldehyde, glyoxal, resorcinol, benzaldehyde, 1-ethyl-3-(3-dimethylaminopropyl)carbodiimide, N-hydroxysuccinimide, N,N-dicyclohexylcarbodiimide, and epoxies. In one embodiment, the crosslinking reagent comprises an epoxy. As used herein, the term "epoxy" means an epoxy resin comprising monomers or short chain polymers having functional epoxide groups. The epoxide groups react with the amine groups and other functional groups to form covalent bonds. Based on the comparison of properties, a protein-cured epoxy network shows comparatively superior properties and can be formulated in a viable method of preparation. Hydrolyzed protein used as hardener/co-reactant in an epoxy formulation yields moisture resistance and thermal properties comparable to those of existing industrial synthetic products. As epoxy-based resins find use as diluents, pigments, fillers and flame retardants in the surface coating, construction, and electrical industry, epoxy-protein based thermosetting resins formulated in this manner may be useful. In one embodiment, the invention comprises crosslinked polymers obtained by the method described herein.

One suitable epoxy is diglycidyl ether of bisphenol A (DGEBA) and known commercially as Araldite™. DGEBA has the formula (2,2-bis[4-(2'3' epoxy propoxy)phenyl]propane) and is derived from the reaction of bisphenol-A and epichlorohydrin. Crosslinking hydrolyzed protein fractions with DGEBA yields polymers characterized by high tensile strength and limited elongation at the breaking point. These mechanical properties are very similar to commercial epoxy-based polymers.

In one embodiment, the polymer may be blended with other polymers or substances to alter the properties of the polymer and any resulting thermoset plastic. For example, it is possible to impart flexibility to DGEBA-based polymers by blending reactive natural or synthetic rubber into the DGEBA prior to curing with the proteins Carboxylic acid synthesized acrylonitrile rubbers, with carboxylic group along the chain and chain ends reacts with epoxy groups of DGEBA and polymerizes altogether through chain extension reactions, to impart flexibility of the backbone molecule. In one embodiment, 10 to 40% by weight of reactive rubber may be incorporated into epoxy resins prior to overall crosslinking with the hydrolyzed protein to obtain various levels of toughness and flexibility of the thermoset plastics.

Other suitable epoxies include an aliphatic polyglycol epoxy (APO) resin or resorcinol diglycidyl ether (RDE). Crosslinking hydrolyzed protein fractions with APO or RDE yields polymers with higher flexibility, lower viscosity, and reduced brittleness. Lower viscosity improves overall processability and potentially increases the amount of proteins incorporated into the matrix.

The crosslinked polymers may be further processed or cured into plastics for use in conventional plastic applications including, but not limited to, packaging, shipping and insulation material. In one embodiment, the invention comprises plastics obtained by the methods described herein.

The cured thermoset polymers produced as described herein, can be used as an adhesive between surfaces such as wood, metal and glass. In one embodiment, the invention comprises a method of using the polymer obtained by the method described herein as an adhesive.

EXAMPLES

The following are specific examples of embodiments and methods of using the present invention. These examples are offered by way of illustration and are not intended to limit the invention in any manner.

Example 1

Preparation of Polymers and Plastics

This example demonstrates how the method of the present invention can be used in preparing polymers and plastics from agricultural proteins.

As the starting material, the feedstock comprised specified risk material obtained from cattle. Thermal hydrolysis was conducted for about forty minutes per cycle at a temperature of at least about 180° C., and at a pressure of about 1,200 kPa using a thermal hydrolysis reactor (Haarslev Inc., Kansas City, Mo., USA; Dupps Company, Germantown, Ohio, USA). The SRM material was suspended in water (33.3%, 50%, 66.7% and 83.3% water by mass) Alkaline hydrolysis was conducted for about 180 minutes per cycle at a temperature of about 150° C., and at a pressure of about 400 kPa using a tissue digestor (Bio-SAFE Engineering, Brownsburg, Ind., USA). The alkaline solution comprised about 15% sodium hydroxide (w/v) in water (33.3%, 50%, 66.7% and 83.3% solution by mass). The protein fraction was then extracted from the hydrolyzed proteins using a combination of salts to precipitate ash, and to retain the protein fraction into aqueous solution.

The physical, chemical and structural characteristics of the protein fraction were found to be correlated to the specific type of hydrolysis.

The molecular weight analysis revealed that alkaline hydrolyzed proteins (at 50% alkaline solution) are severely cleaved to a molecular weight of less than 35 kDa due to the catalytic property of the hydroxide solution. Thermal hydrolyzed proteins have comparatively wider range of molecular weight, with an average molecular weight of less than about 66 kDa.

Sodium dodecyl sulfate polyacrylamide gel electrophoresis (SDS-PAGE) and size exclusion high performance liquid chromatography (SEC-HPLC) may be used to evaluate the degree of protein cleavage and measure molecular size distribution of hydrolyzed products.

A specified risk material (SRM) hydrolyzate typically has a strong pungent smell and a color ranging from dark red in the case of thermal hydrolysis to dark brown for the alkaline hydrolysis. Both thermal and alkaline hydrolysis break down clumps of the tissues into a soluble fraction and a residue rich in bone fragments.

Figure 18:
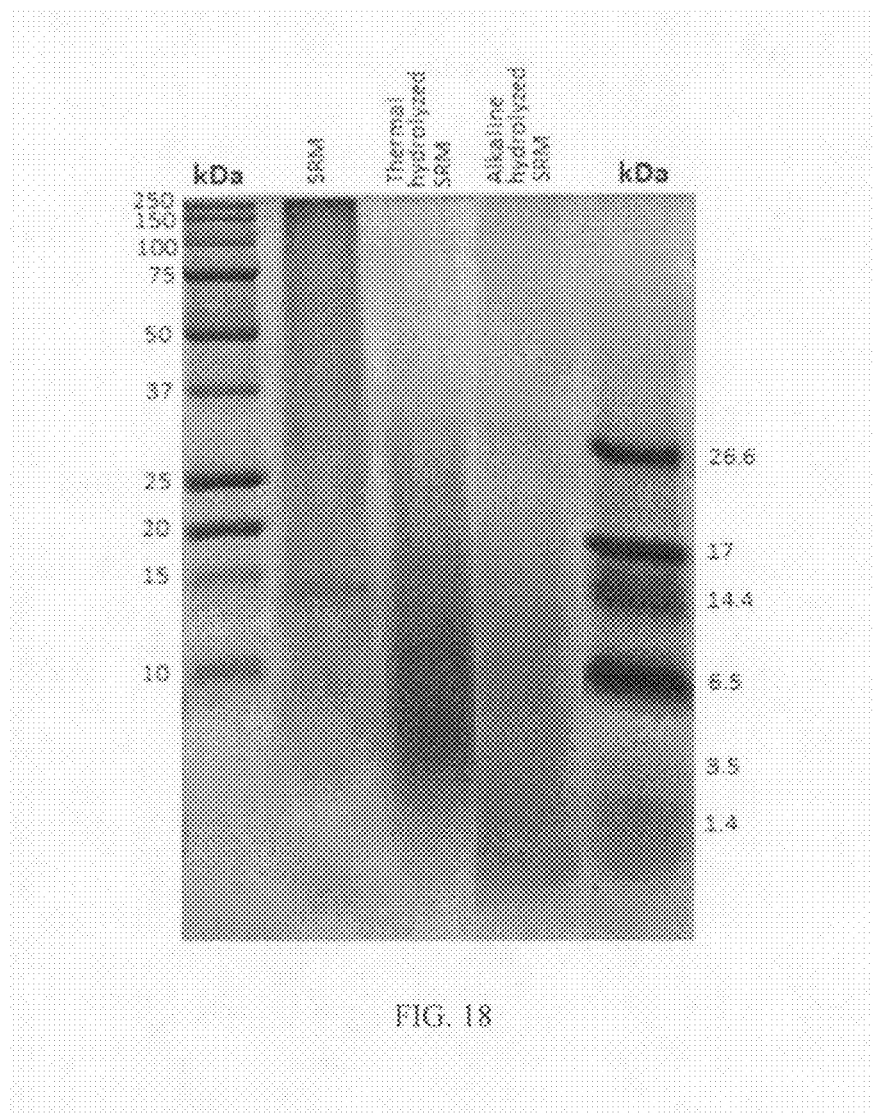
FIG. 18 shows SDS PAGE of SRM and its thermal and alkaline hydrolyzate at 50% solvent concentration.

When SDS-PAGE is conducted in 50% water, unhydrolyzed SRM proteins are characterized by a relatively broad size distribution, with a predominance of large molecular sizes (greater than about 100 kDa). Proteins from unhydrolyzed SRM are also characterized by two bands appearing at about 18 and 14 kDa, possibly representing hemoglobin subunits. Protein cleavage is evident in both alkaline and thermal hydrolysis samples as most of the hydrolyzed proteins are concentrated below the 25 kDa marker, as shown in FIG. 18. Whereas the proteins from thermal hydrolyzed SRM smear primarily between 15 and 5 kDa, the proteins from alkaline hydrolysis smeared to less than 1 kDa. Alkaline treatment is more severe than the thermal treatment, leading to a higher degree of cleavage. The presence of alkali is known to exert a catalytic effect on the hydrolysis reaction, increasing the likelihood of greater protein cleavage.

Figure 19:
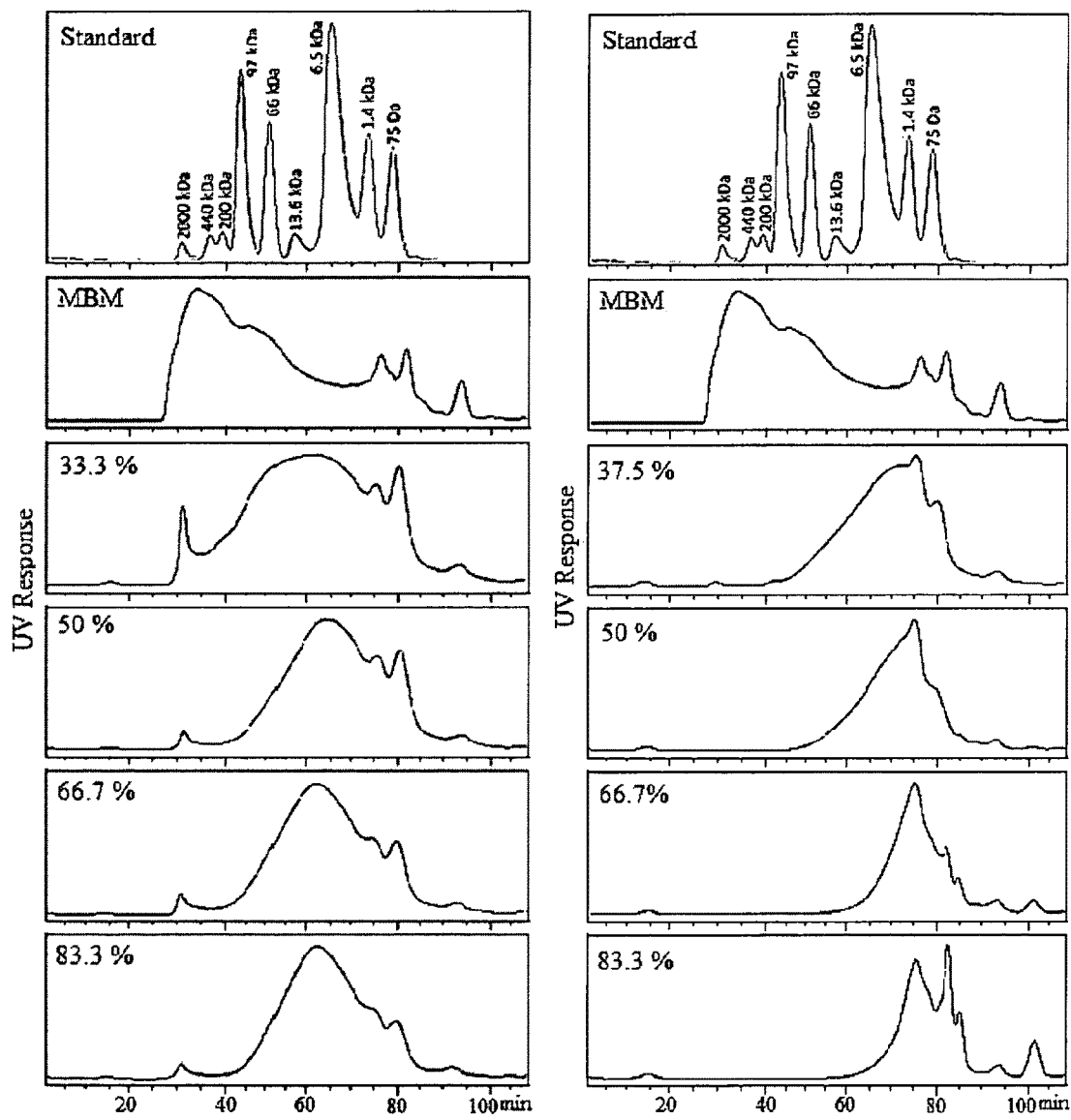
FIG. 19 shows SEC-HPLC of a) thermal hydrolyzed SRM in 33.33%, 50.00%, 66.67% and 83.33% water to the total mass b) alkaline hydrolyzed SRM in 37.50%, 50.00%, 66.67% and 83.33% alkaline solution (15% w/v NaOH) to the total mass.

With both thermal and alkaline hydrolysis, increasing relative amounts of water translated into a greater degree of protein cleavage and yielded hydrolyzate with a relatively narrower distribution molecular weights compared with the material pre-hydrolysis, as shown in FIG. 19. It should be noted that at each given water dilution level, the alkaline protocol produced smaller and more homogenous hydrolyzate. At 83.3% total alkali solution containing 15% w/v NaOH; substantially all of the proteins were broken down to short peptides below 10 kDa, and with a relatively narrow molecular weight distribution range owing to the more water and NaOH per a given weight of SRM.

Thermal hydrolysis was also performed at 180°, 200°, 220° C., 240° and 260° C. at 1200 kPa for a period of at least 40 minutes per cycle. Elevated temperatures resulted in increased hydrolysis, evidenced by molecular size distributions below 49.3, 24.6, 9.0, 5.4, and 3.5 kDa, respectively.

The amino acid profile was obtained using reversed-phase HPLC. The protein fraction comprised functional groups including primary amine (—NH$_2$), carboxyls (—COOH), sulfhydryls (—SH), hydroxyl (—OH), and carbonyls (—CHO). The functional groups were positioned on the side chain of each amino acid or the end of each main chain.

Figure 3:
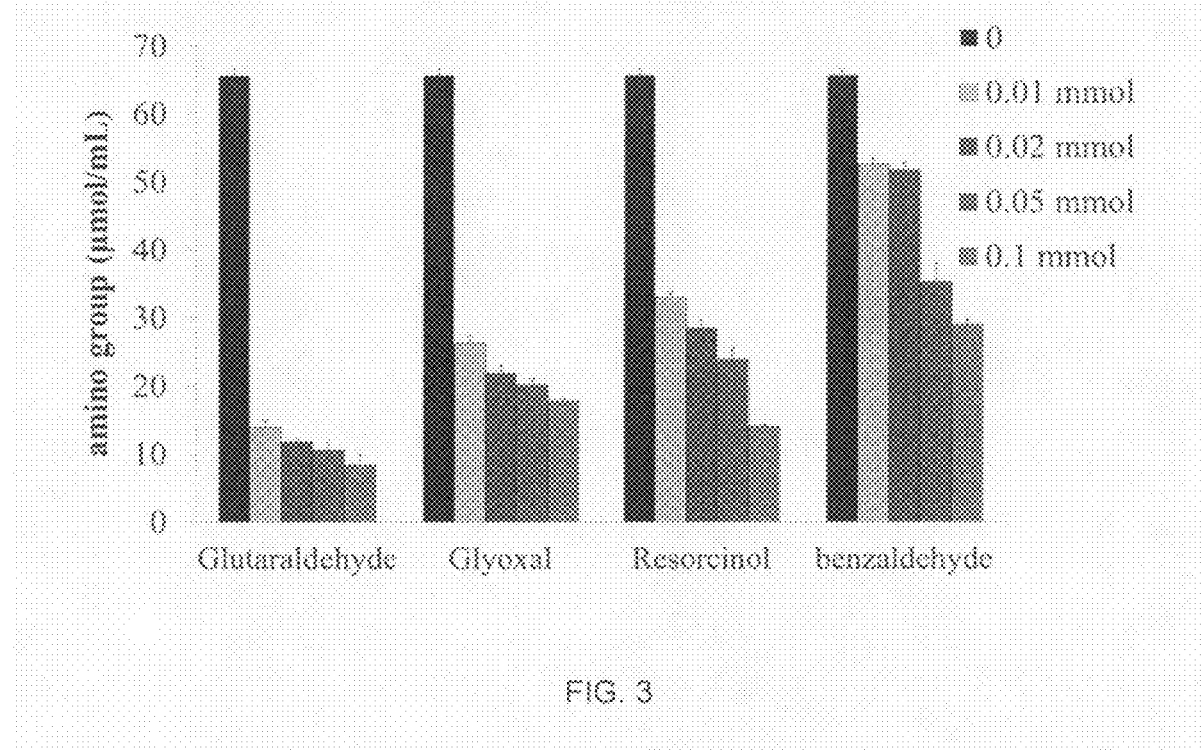
FIG. 3 is a graph showing total free amines as a function of the crosslinking reagent and molar concentration.

Both thermal and alkaline hydrolysis yielded protein fractions which are amenable to crosslinking, providing two distinct routes to prepare final products having different properties. A functional group study showed that most functional groups of protein survived the conditions of both thermal and alkaline hydrolysis. The reduction in functional groups was used to measure the level of crosslinking of proteins with various agents (i.e., glutaraldehyde, glyoxal, resorcinol, and benzaldehyde) at various molar concentrations (i.e., 0 mmol, 0.01 mmol, 0.02 mmol, 0.05 mmol, and 0.1 mmol). A linear reduction of amine group was observed as the molar concentration of each of the crosslinking reagents was increased (FIG. 3).

Figure 4:
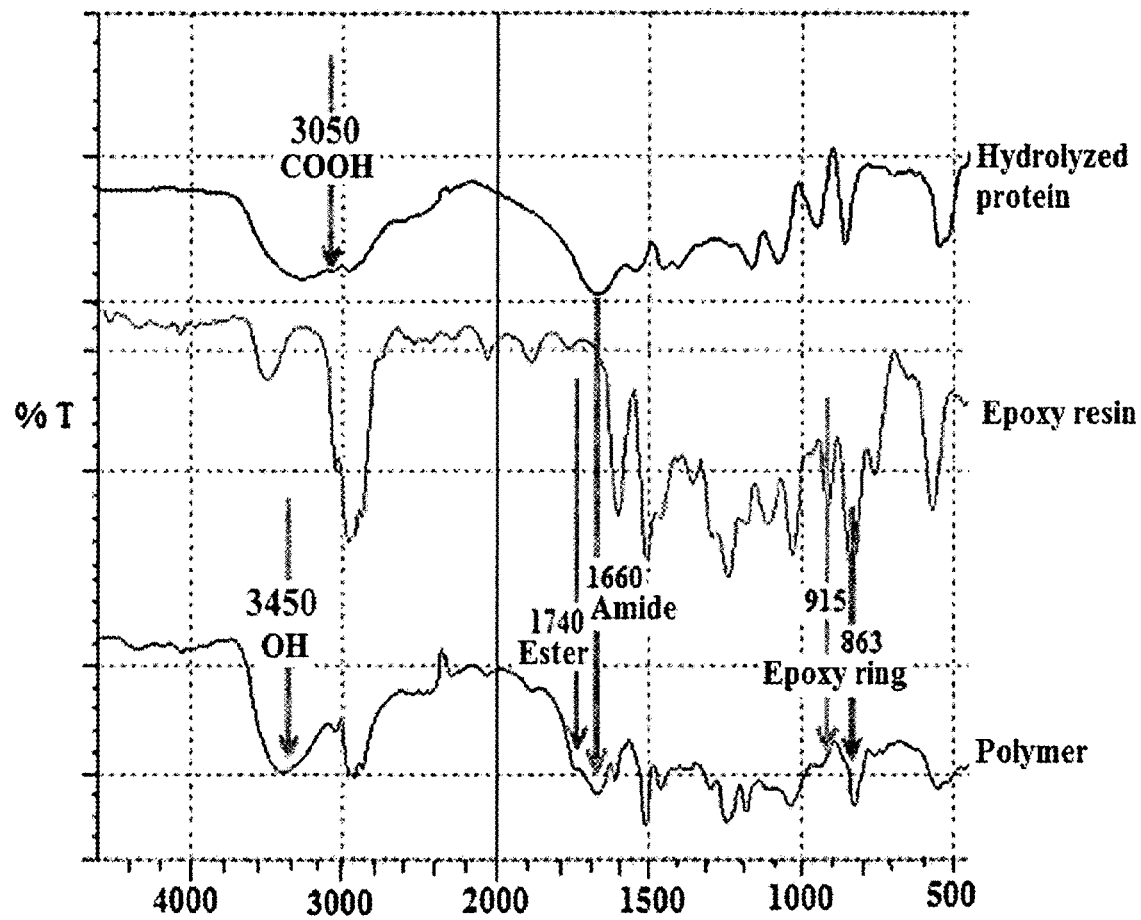
FIG. 4 is a Fourier transform infrared spectra of hydrolyzed protein, epoxy resin, and epoxy resin crosslinked polymer.

FIG. 4 is a Fourier transform infrared spectra of hydrolyzed protein, epoxy resin, and epoxy resin crosslinked polymer. The spectra showed carboxylic acid and epoxy ring reduction and the formation of new ester bonds. Epoxy, being reactive to several protein functional groups, exhibited superior crosslinking property.

Example 2

Sodium Dodecyl Sulfate Polyacrylamide Gel Electrophoresis (SDS-PAGE)

Proteinacious material is extracted by solubilizing 0.5 g of SRM and 1 g of the hydrolyzed SRM in 10 mL of 2.5% (w/v) SDS and Milli-Q water, respectively and vortexing followed by centrifugation at 15,700×g each for 5 min. The prepared protein extracts are fractionated using a mini-protean II electrophoresis unit (Bio-Rad Laboratories, Richmond, Calif., USA) tricine-SDS PAGE. The stacking gel and the resolving gel contain 4% and 10% polyacrylamide, respectively. Protein standards with molecular weight ranges of 10-250 kDa and 1.4-26.6 kDa (Bio-Rad Laboratories, Inc., Hercules, Ca, USA) are utilized and Coomassie Brilliant Blue G-250 is used as a tracking dye. After completion, the gels are stained with a solution containing 0.1% Coomassie Brilliant Blue, 40% methanol, and 7% acetic acid, and then de-stained using a solution of 40% methanol and 7% acetic acid.

Example 3

Size Exclusion High Performance Liquid Chromatography (SEC-HPLC)

SEC-HPLC is used to evaluate the level of protein cleavage and molecular weight distribution of SRM hydrolyzates as a function of the hydrolysis temperature. Samples are prepared from each hydrolysis by solubilizing the lyophilized protein hydrolyzates in the mobile phase to yield 30 mg/mL protein. The solubilized hydrolyzate solutions are then centrifuged at 15,400×g for 5 min, pH neutralized, and filtered through a 0.22 µm filter (Millipore, Bedford, Mass., USA). The prepared samples are then loaded into a Varian Prostar 210 HPLC with a variable wavelength UV detector. The injection volume is 100 µL. Two size exclusion columns in series (Superdex 200 10/300 GL and Superdex Peptide 10/300 GL, GE Healthcare Biosciences AB, Uppsala, Sweden) are used for hydrolyzate size separation. The chromatographic system is calibrated with external standards dissolved in buffer solution: albumin (66 kDa), carbonic anhydrase (29 kDa), cytochrome C (13.6 kDa), aprotinin (6.5 kDa), vitamin B-12 (1.36 kDa) and glycine (75 Da). The mobile phase is 0.15 M Na$_2$HPO$_4$ (adjusted to pH 9 with 1 N NaOH) in HPLC grade water (Milli-Q System; Millipore, Bedford, Mass.) containing 5% acetonitrile at a flow rate of 0.5 mL/min at room temperature. The eluted compounds are detected by UV absorbance at 210 nm.

Example 4

Use of RDE as Crosslinking Reagent

This example demonstrates how the method of the present invention can use resorcinol diglycidyl ether (RDE) as a crosslinking reagent.

Figure 5:
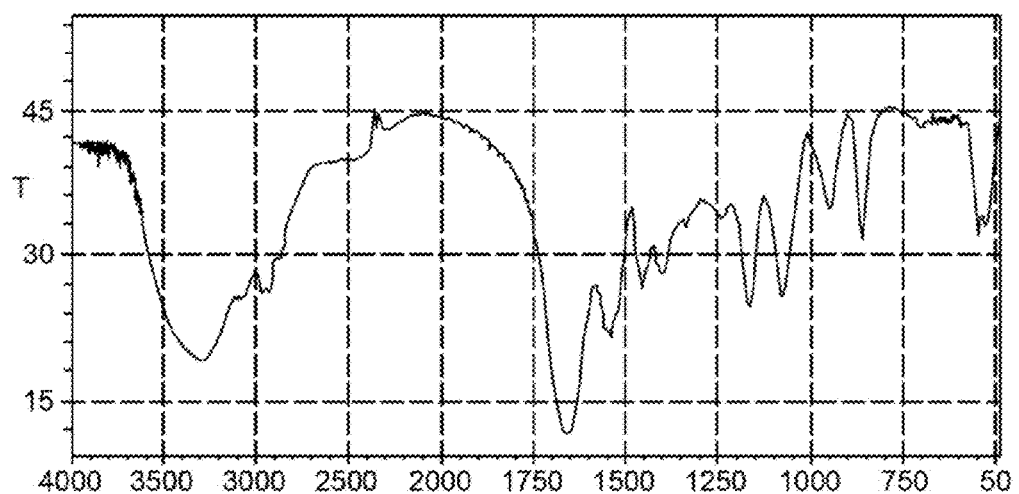
FIG. 5 is a Fourier transform infrared spectra of hydrolyzed protein prior to crosslinking.
Figure 6:
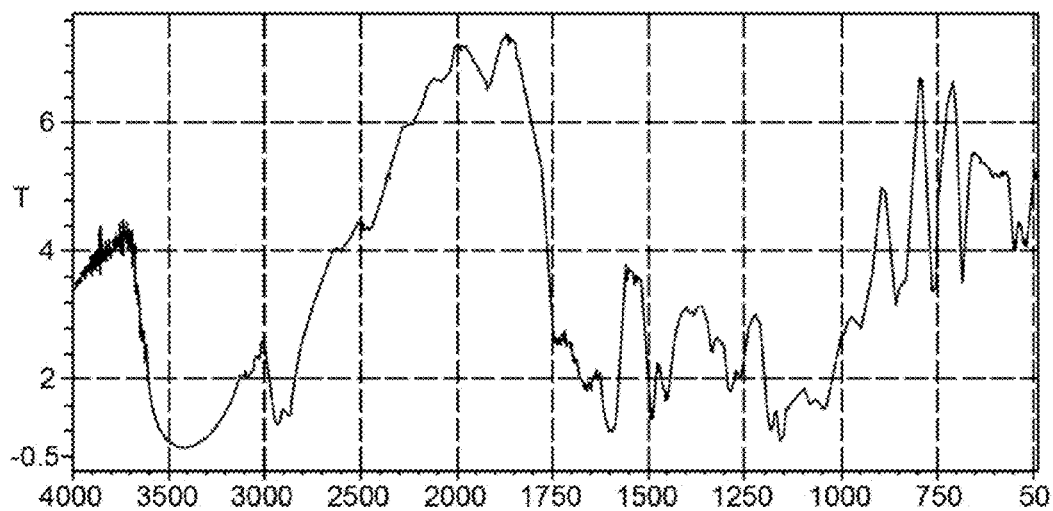
FIG. 6 is a Fourier transform infrared spectra of the hydrolyzed protein of FIG. 5 after crosslinking with resorcinol diglycidyl ether.

FIG. 5 is a Fourier transform infrared spectra of hydrolyzed protein prior to crosslinking. FIG. 6 is a Fourier transform infrared spectra of the hydrolyzed protein of FIG. 5 after crosslinking with RDE. The broad absorption band in the range of 3200-3500 cm$^{-1}$ corresponds to the hydroxyl (O—H) of the hydrolyzed proteins whereas the band at around 1525 cm$^{-1}$ can be attributed to the amine group (N—H) of the protein chain. A comparison of FIGS. 5 and 6 depicts how both groups have disappeared following crosslinking, demonstrating that epoxy can cap both reactive moieties.

Example 5

Method of Using Proteinaceous Polymers as an Adhesive

Proteinaceous adhesive formulations were prepared using hydrolyzed protein containing 91% (dry basis) protein extracted from specified risk material thermally hydrolyzed as described in Example 1 above (CFIA, 2009). The extract was freeze-dried and milled into powder. The hydrolyzed protein was mixed with one of two crosslinking reagents. In the first case, the hydrolyzed protein was dispersed in solutions of glutaraldehyde (Fisher Scientific, 50%). The protein concentrations varied from 0 to 30 percent by weight, and the glutaraldehyde concentration in the solutions varied from 0 to 50 percent. The dispersions were agitated for 3 hours at 250 rpm until a homogeneous solution was obtained. The pH of the adhesive formulations were adjusted to neutral using 0.5 N NaOH and 0.1N HCl solutions. In the second case, the hydrolyzed protein was dispersed in solutions of Diglycidyl Ether of Bisphenol A (DGEBA) epoxy resin (Sigma-Aldrich, epoxide equivalent weight, 172-185 Da). The protein concentrations in the DGEBA varied from 0 to 40 percent by weight, the remaining being epoxy resin.

In addition, to serve as an industrial benchmark for the proteinaceous adhesive formulations, a urea formaldehyde adhesive was prepared by dispersing about 50 g of urea in 100 mL of aqueous formaldehyde. (The reaction of urea and formaldehyde involves condensation between the nucleophilic nitrogen of urea with the electrophilic carbonyl carbon of formaldehyde.) The mixture was stirred at 60° C. for 15 min and the pH was adjusted to 8.5 by adding drops of 0.5

N analytical grade NaOH (Fisher Scientific), and refluxed for 30 minutes. A white semi-solid urea formaldehyde polymer was produced.

Specimens were prepared to test the adhesive bond strength of the adhesive formulations. The test specimens were made by obtaining hardwood plywood veneer (oak, Columbia Forest Products) from a Home Depot store in Edmonton, Alberta and cutting the veneer into rectangular pieces having dimensions of 3×20×50 mm (thickness, width and length) (FIG. 7). Each of the formulated adhesive slurries was brushed onto each surface of the test specimens in the amount of about 15 mg/cm$^2$ to wet the glued area of the test specimens (FIG. 8). The specimens were allowed to equilibrate for 10 minutes and then pressed at varying temperature and pressure combinations using a thermal press (Model 3890 Auto 'M', Carver, Wabash, Ind.). In the case of the protein-glutaraldehyde adhesive formulation, the pressing temperatures ranged from 100° C. to 150° C. and the pressures ranged from 1 MPa to 5 MPa. In the case of the protein-DGEBA adhesive formulation, pressing times ranged from 10 to 60 minutes and pressing temperatures ranged from 100° C. to 200° C. Preliminary study of protein crosslinking with epoxy using differential scanning calorimeter showed high temperature requirement to complete the curing, unless it is catalyzed. The glued test specimens were conditioned at 23° C. and 50% relative humidity for 7 days after hot pressing. The conditioned specimens were tested for dry shear strength in accordance with ASTM Standard Method D2339 using Instron 5967 (Norwood, Mass., USA) equipped with a 5 kN load cell at a crosshead speed of 1 mm/min. The shear strength was calculated as the average determination from quintuplicate specimens.

Figure 9:
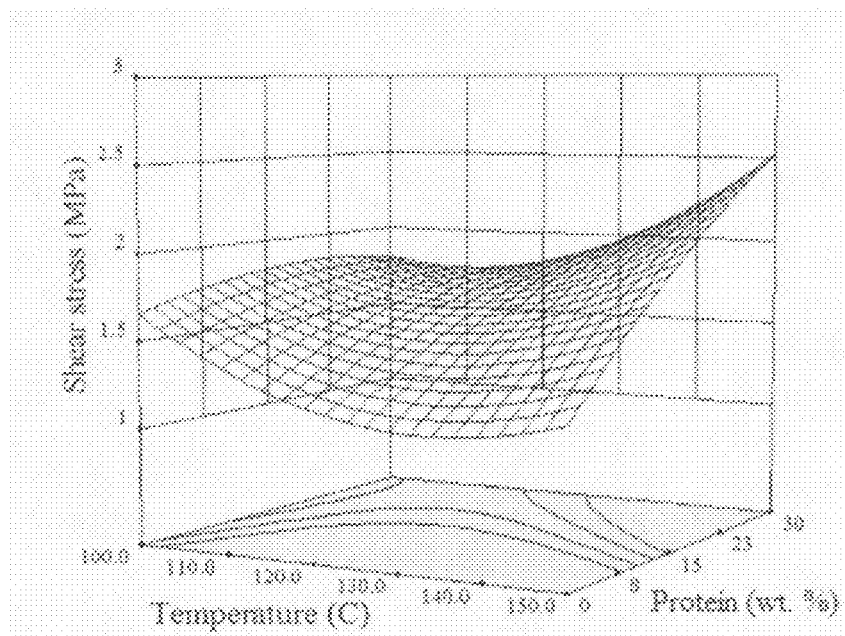
FIG. 9 is a graph showing the effect of pressing temperature and protein concentration on the adhesive bond strength of one embodiment of a protein-glutaraldehyde adhesive formulation of the present invention.
Figure 10:
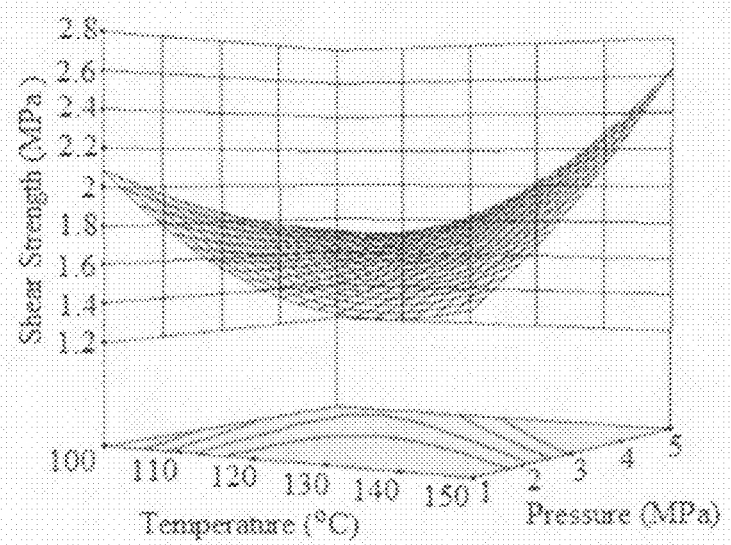
FIG. 10 is a graph showing the effect of pressing temperature and pressure on the adhesive bond strength of one embodiment of a protein-glutaraldehyde adhesive formulation of the present invention.

With respect to the protein-glutaraldehyde adhesive formulations, the adhesive bond strength was comparable and in some cases greater than the adhesive bond strength of the urea formaldehyde adhesive formulation, which was found to be 1.97 MPa. FIGS. 9 to 14 illustrate the effect of pressing temperature and pressure, glutaraldehyde concentration and protein concentration on the adhesive bond strength of the protein-glutaraldehyde adhesive formulations. (Statistical analysis (not shown here) indicated that temperature and pressure, protein and glutaraldehyde concentration were interacting parameters, so it was impossible to separately observe the influence of one parameter without the other in this study.) Referring to FIG. 9, higher protein concentrations generally favoured higher adhesive bond strength. Formulations with protein concentrations exceeding 25% (w/v) were found to have high viscosity that will in effect increase the contact angle of the adhesive with the wood surface, which leads to unfavourable dispersion properties of the adhesive, Referring to FIG. 10, higher pressure generally favoured higher adhesive bond strength. Pressures above 4 MPa started to damage the plywood test specimen.

Figure 11:
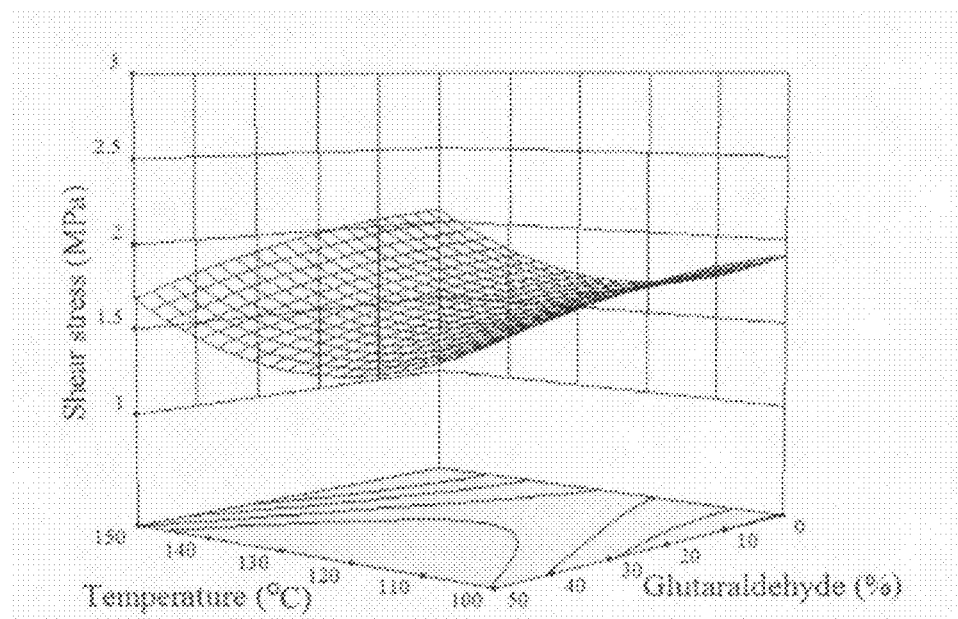
FIG. 11 is a graph showing the effect of pressing temperature and glutaraldehyde concentration on the adhesive bond strength of one embodiment of a protein-glutaraldehyde adhesive formulation of the present invention.
Figure 12:
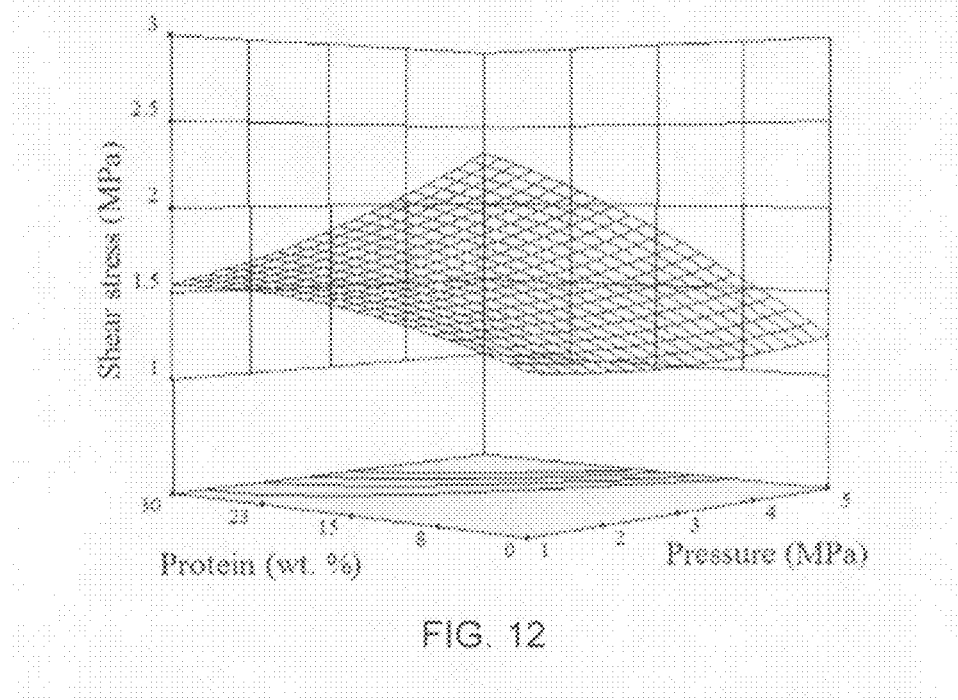
FIG. 12 is a graph showing the effect of protein concentration and pressing pressure on the adhesive bond strength of one embodiment of a protein-glutaraldehyde adhesive formulation of the present invention.
Figure 13:
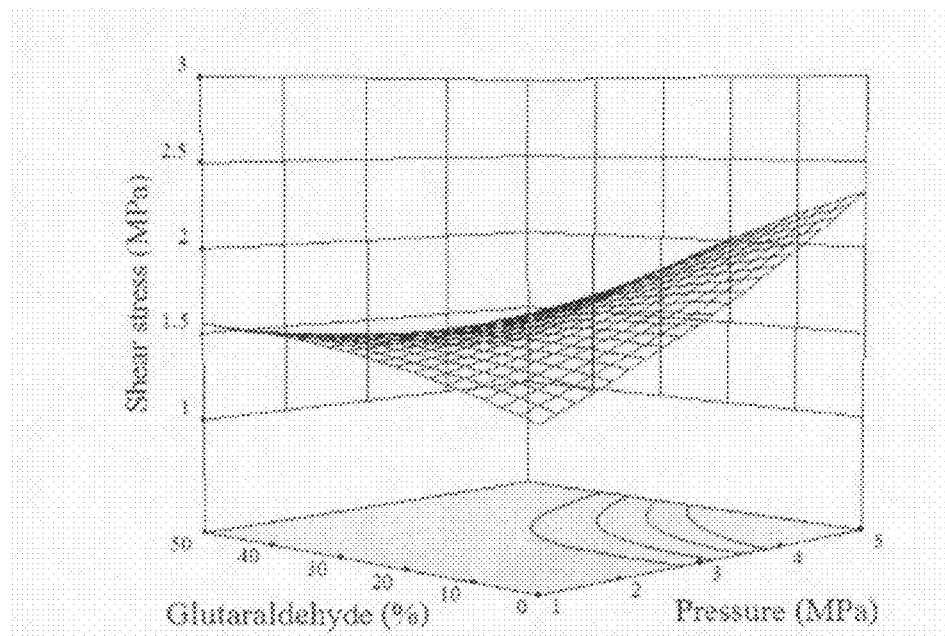
FIG. 13 is a graph showing the effect of glutaraldehyde concentration and pressing pressure on the adhesive bond strength of one embodiment of a protein-glutaraldehyde adhesive formulation of the present invention.
Figure 14:
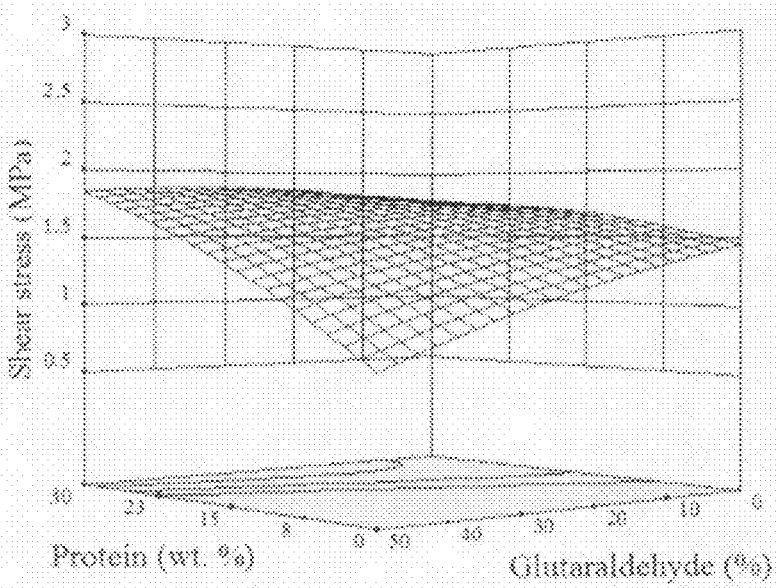
FIG. 14 is a graph showing the effect of protein concentration and glutaraldehyde concentration on the adhesive bond strength of one embodiment of a protein-glutaraldehyde adhesive formulation of the present invention.
Figure 15:
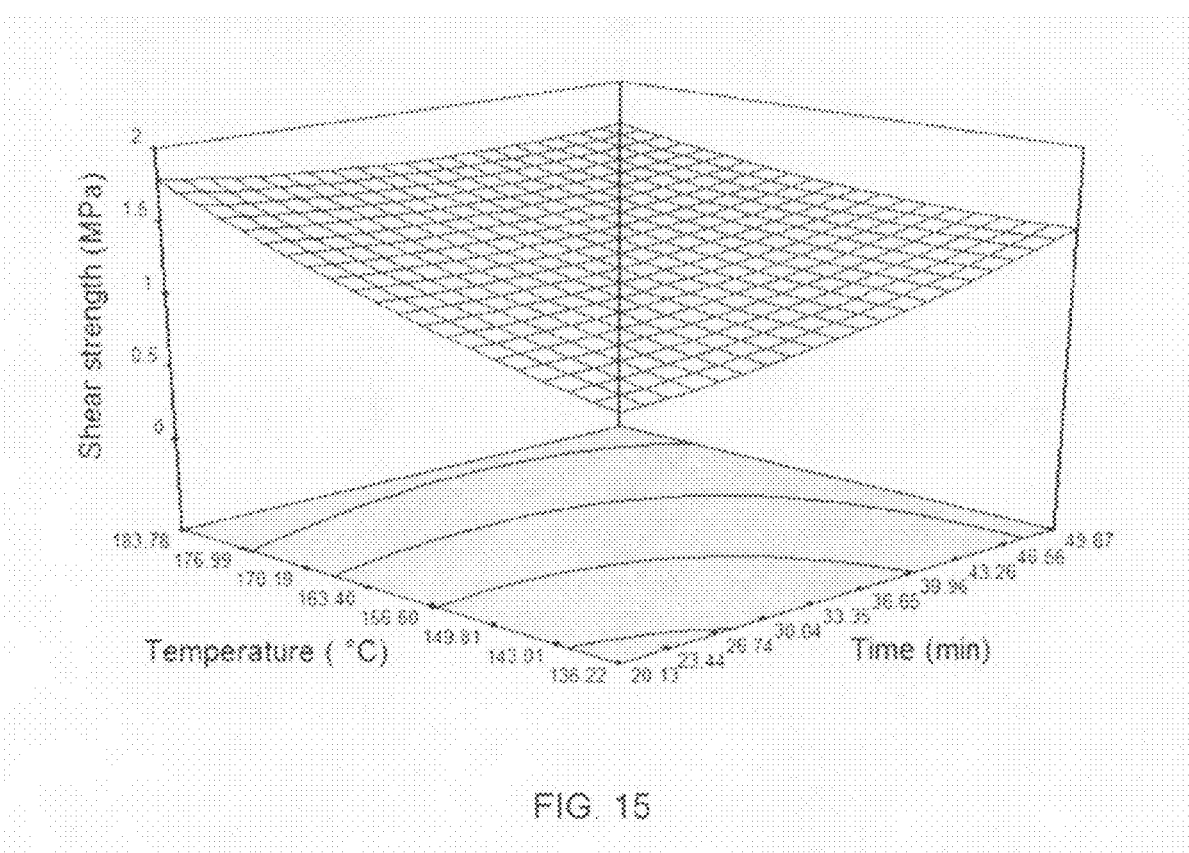
FIG. 15 is a graph showing the effect of pressing temperature and time on the adhesive bond strength of one embodiment of a protein-DGEBA adhesive formulation of the present invention.
Figure 16:
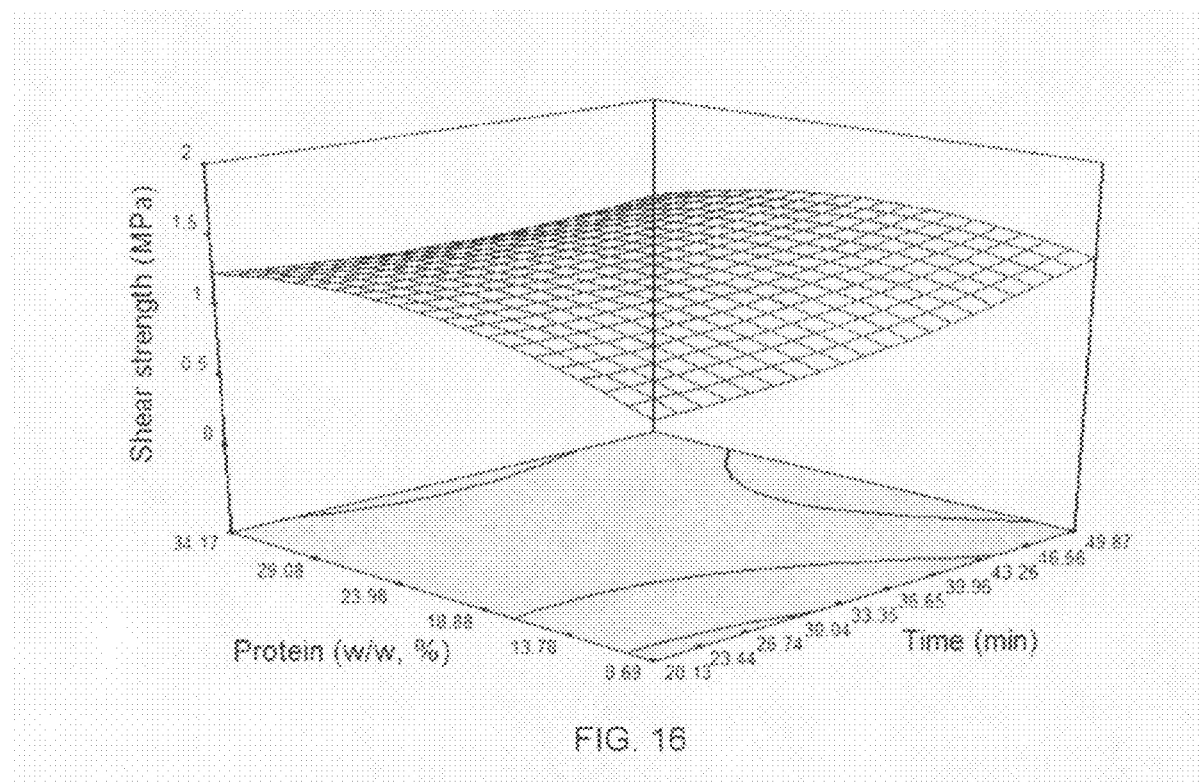
FIG. 16 is a graph showing the effect of protein concentration and pressing time on the adhesive bond strength of one embodiment of a protein-DGEBA adhesive formulation of the present invention.
Figure 17:
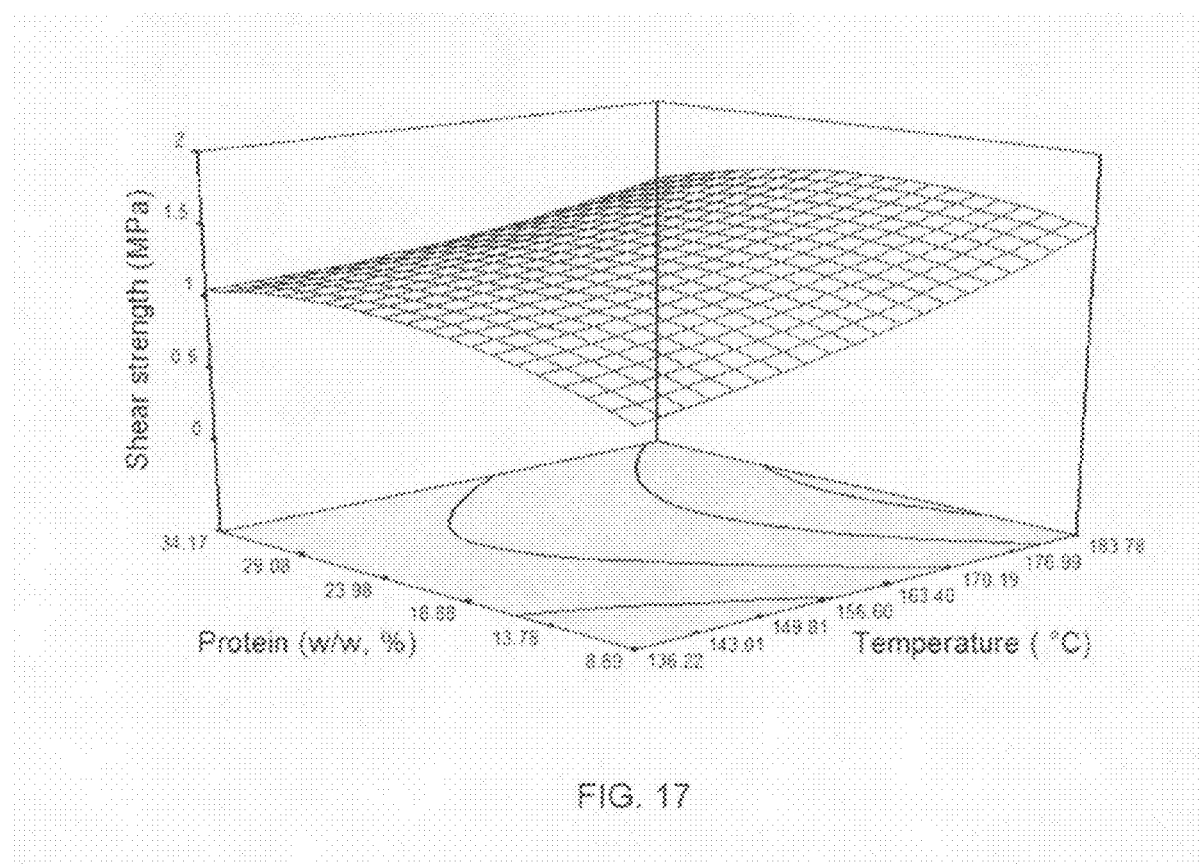
FIG. 17 is a graph showing the effect of protein concentration and pressing temperature on the adhesive bond strength of one embodiment of a protein-DGEBA adhesive formulation of the present invention.

With respect to the protein-DGEBA adhesive formulations, the adhesive bond strength was of the same order of magnitude as the urea formaldehyde adhesive and in some cases less. The lack of strength might be attributed to the poor penetration of epoxy protein adhesive into the wood surface owing to its high viscosity. However, the water resistance of epoxy based adhesives bond is expected to be superior to the rest of the protein-glutaraldehyde or urea formaldehyde adhesives formulations. FIGS. 11, 12 and 13 illustrate the effect of pressing temperature, time and protein concentration on the adhesive bond strength of the protein-DGEBA adhesive formulations. Longer pressing time and higher pressing temperature during bonding favored greater adhesive bond strength. This could be due to completion of protein curing with epoxy resin. Referring to FIGS. 12 and 13, increasing total protein concentration up to about 24% per weight of epoxy in the adhesive formulation increased the adhesive bond strength, but increases in total protein concentration above 24% per weight of epoxy reduced the adhesive bond strength. The decrease of the adhesive bond strength for protein concentrations above 24% per weight of epoxy might be attributed to the high viscosity of the mix, leading to poor penetration depth of the adhesive.

Exemplary embodiments of the present invention are described in the above Examples, which are set forth to aid in the understanding of the invention, and should not be construed to limit in any way the scope of the invention as defined in the claims which follow thereafter.

All experiments were performed in a Biosafety Level II laboratory (University of Alberta, Edmonton, Canada) operating under a Canadian Food Inspection Agency permit for handling specified risk material.

REFERENCES

The following references are incorporated herein by reference (where permitted) as if reproduced in their entirety. All references are indicative of the level of skill of those skilled in the art to which this invention pertains.

ASTM D2339-98, Standard Test Method for Strength Properties of Adhesives in Two-Ply Wood Construction in Shear by Tension Loading ASTM, West Conshohocken, 15 Jun. 2002.

CFIA. 2009 Bovine Spongiform Encephalopathy Manual of Procedures. (accessed Sep. 9, 2010).

Wilson, J. H.; Kaye; G. I.; Hahn, R. L.; Weber, P. B. and Morris, K. A. System for treating infectious waste matter, U.S. Pat. No. 7,910,788, issued Mar. 22, 2011.

Wilson, J. H.; Kaye, G. I.; Hahn, R. L.; Weber, P. B. and Morris, K. A. System and method for treating infectious waste matter, U.S. Pat. No. 7,829,755, issued Nov. 9, 2010.

Wilson, J. H.; Kaye, G. I.; Hahn, R. L.; Weber, P. B. and Morris, K. A. Method for treating infectious waste matter. U.S. Pat. No. 7,183,453, issued Feb. 27, 2007.

Park, S. K., Bae, D. H., Hettiarachchy, N. S. 2000. Protein Concentrate and adhesives from meat and bone meal. JAOCS. 77(11), 1223-1227.

What is claimed is:

1. An adhesive polymer comprising hydrolyzed specified risk material (SRM) proteins including animal brain proteins, cross-linked by a cross-linking agent.

2. The polymer of claim 1 wherein the cross-linking agent comprises glutaraldehyde, glyoxal, resorcinol, benzaldehyde, 1-ethyl-3-(3-dimethylaminopropyl)carbodiimide, N-hydroxysuccinimide, N,N-dicyclohexylcarbodiimide, or an epoxy.

3. The polymer of claim 1 wherein the hydrolyzed SRM proteins have an average molecular weight of less than about 100 kDa.

4. The polymer of claim 3 wherein the hydrolyzed SRM proteins have an average molecular weight of less than about 70 kDa.

5. The polymer of claim 4 wherein the hydrolyzed SRM proteins have an average molecular weight of less than about 35 kDa.

6. The polymer of claim 1 blended with a natural or synthetic rubber.

7. A thermoset plastic comprising a polymer comprising cross-linked hydrolyzed SRM proteins including animal brain proteins.

* * * * *